US012644801B2

(12) United States Patent

McGhee et al.

(10) Patent No.: US 12,644,801 B2

(45) Date of Patent: Jun. 2, 2026

(54) METHODS PROVIDING SAMPLE COLLECTION USING SAMPLE COLLECTION FILMS AND RELATED DEVICES, FILMS, AND REELS

(71) Applicant: The Government of the United States of America, as represented by the Secretary of the Navy, Arlington, VA (US)

(72) Inventors: Eric O. McGhee, Alexandria, VA (US); Alexander J. McGhee, Madison, WI (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 366 days.

(21) Appl. No.: 18/229,454

(22) Filed: Aug. 2, 2023

(65) Prior Publication Data

US 2025/0020552 A1     Jan. 16, 2025

Related U.S. Application Data

(60) Provisional application No. 63/525,787, filed on Jul. 10, 2023.

(51) Int. Cl.
*G01N 1/28*        (2006.01)
*B01L 3/00*        (2006.01)
(Continued)

(52) U.S. Cl.
CPC ............ *G01N 1/2813* (2013.01); *B01L 3/505* (2013.01); *G01N 1/312* (2013.01);
(Continued)

(58) Field of Classification Search
CPC ................ G01N 1/2813; G01N 1/312; G01N 33/48764; G01N 35/00009;
(Continued)

(56) References Cited

U.S. PATENT DOCUMENTS 3,675,488 A * 7/1972 Viktora ............ G01N 35/00009
436/817
4,218,421 A * 8/1980 Mack, Jr ................ G01N 31/22
422/561

(Continued)

FOREIGN PATENT DOCUMENTS

EP          1710565 A1 * 10/2006   ....... A61B 5/150854
WO     WO-2005032372 A1 *  4/2005   ......... A61B 5/14532
(Continued)

OTHER PUBLICATIONS

EP-1710565-A1, English Translation (Year: 2006).*
(Continued)

*Primary Examiner* — Ryan D Walsh

(74) *Attorney, Agent, or Firm* — US Naval Research Laboratory; Scott C. Hatfield

(57) ABSTRACT

Methods of collecting liquid samples are disclosed. According to some embodiments, a portion of a sample collection film is unrolled from a first reel to a position adjacent a sample dispenser. A liquid sample is dispensed from the sample dispenser onto the portion of the sample collection film. After dispensing the liquid sample onto the portion of the sample collection film, the portion of the sample collection film is rolled onto a second reel. Related sample collection devices, films, and reels are also disclosed.

19 Claims, 9 Drawing Sheets

(51) Int. Cl.
| | |
|---|---|
| *G01N 1/31* | (2006.01) |
| *G01N 33/487* | (2006.01) |
| *G01N 35/00* | (2006.01) |

(52) U.S. Cl.
CPC . *G01N 33/48764* (2013.01); *G01N 35/00009* (2013.01); *G01N 2001/2826* (2013.01); *G01N 2035/00019* (2013.01)

(58) Field of Classification Search
CPC .. G01N 2001/2826; G01N 2035/00019; B01L 3/505
See application file for complete search history.

(56) References Cited

U.S. PATENT DOCUMENTS

| | | | | |
|---|---|---|---|---|
| 4,959,976 A | * | 10/1990 | Matsuda | G01N 35/00009 62/271 |
| 5,009,850 A | * | 4/1991 | Bell | B01L 99/00 436/166 |
| 5,077,010 A | * | 12/1991 | Ishizaka | G01N 35/00009 422/62 |
| 5,096,828 A | * | 3/1992 | Ishizaka | G01N 35/00009 422/66 |
| 5,508,200 A | * | 4/1996 | Tiffany | G01N 35/00009 436/166 |
| 11,287,426 B2 | | 3/2022 | Kamei | |
| 11,889,813 B2 | * | 2/2024 | Dallerup Rasmussen | A01J 5/0131 |
| 2004/0086869 A1 | * | 5/2004 | Schembri | B01J 19/0046 506/9 |
| 2010/0286564 A1 | * | 11/2010 | Roe | A61B 5/150503 600/584 |

FOREIGN PATENT DOCUMENTS

| | | | | |
|---|---|---|---|---|
| WO | WO-2015008281 A1 | * | 1/2015 | G01N 35/00009 |
| WO | WO-2018236271 A1 | * | 12/2018 | A01J 5/0131 |

OTHER PUBLICATIONS

WO-2005032372-A1, English Translation (Year: 2005).*
WO-2015008281-A1, English Translation (Year: 2015).*
WO-2018236271-A1, English Translation (Year: 2018).*
Bio-Rad Laboratories, Inc., "BioFrac (TM) Fraction Collector," https://www.bio-rad.com/en-us/product/biofrac-fraction-collector?ID=ec82e7b4-919e-428b-ac03-9adf1f50a48e, USA, 14 pages, downloaded Jun. 8, 2023.
Brandel, "Continuous Small-Volume Fractionator: A Revolutionary Method for Collecting and Fixing Small Volumes," www.brandel.com/literature/BrandelContFractionator.pdf, Gathersburg, Maryland, USA, 2 pages, downloaded May 19, 2023.
Nishat et al., "Paper-Based Microfluidics: Simplified Fabrication And Assay Methods," Sensors and Actuators: B. Chemical, Elsevier B.V., Netherlands, vol. 336, Jun. 2021, 129681, 20 pages.
Liu et al., "Roll-to-roll wax transfer for rapid and batch fabrication of paper-based microfluidics," Springer-Verlag GmbH, Germany, Dec. 10, 2019, Article No. 6, 7 pages.

* cited by examiner

FIG. 1B
FIG. 1C
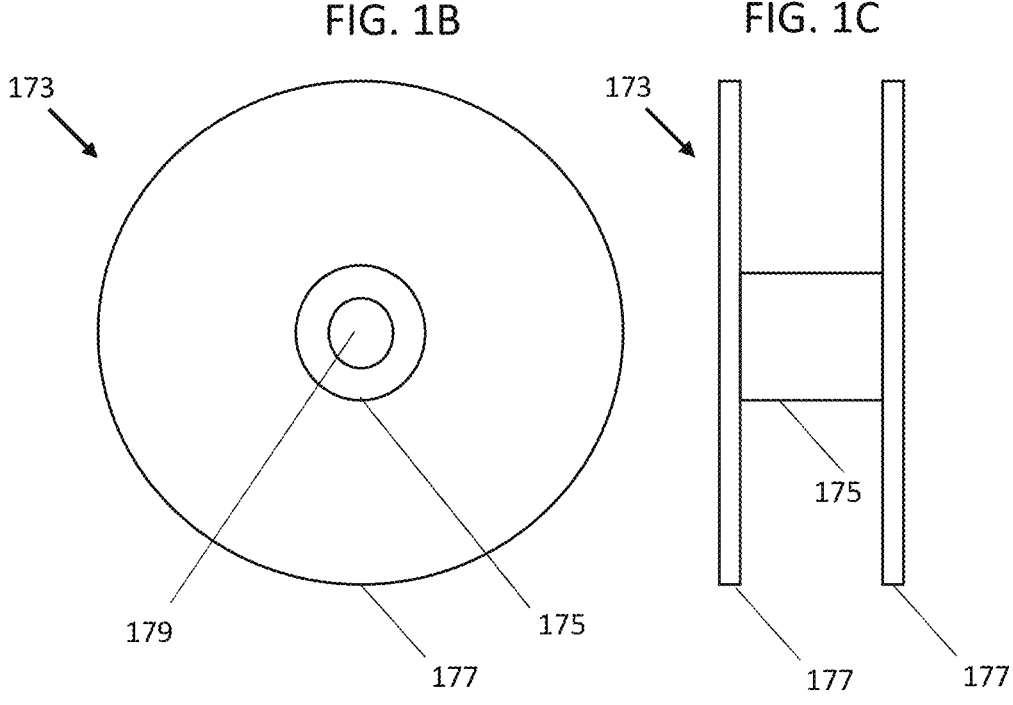
FIG. 1D
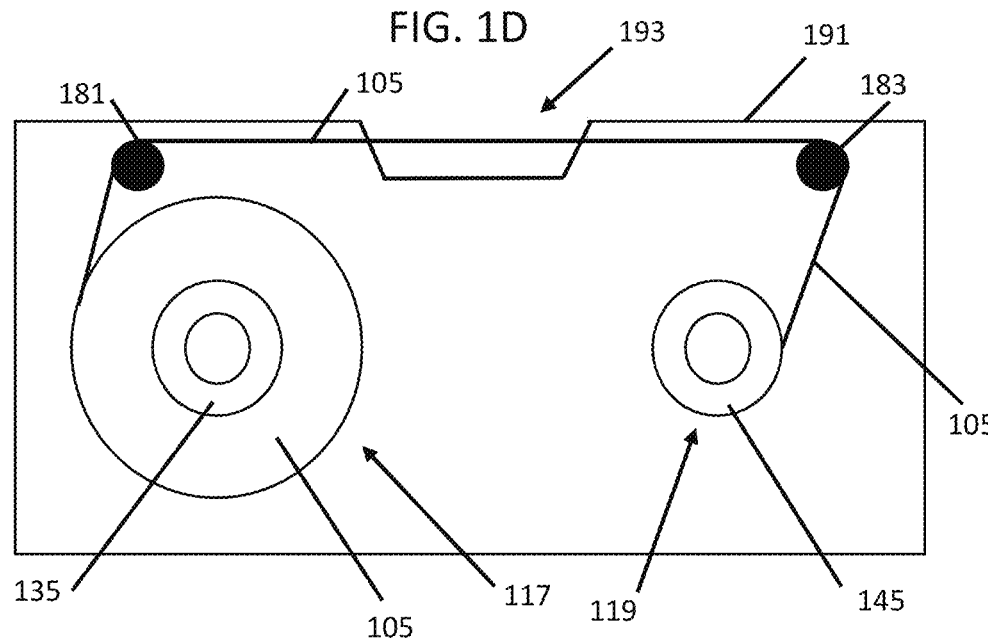

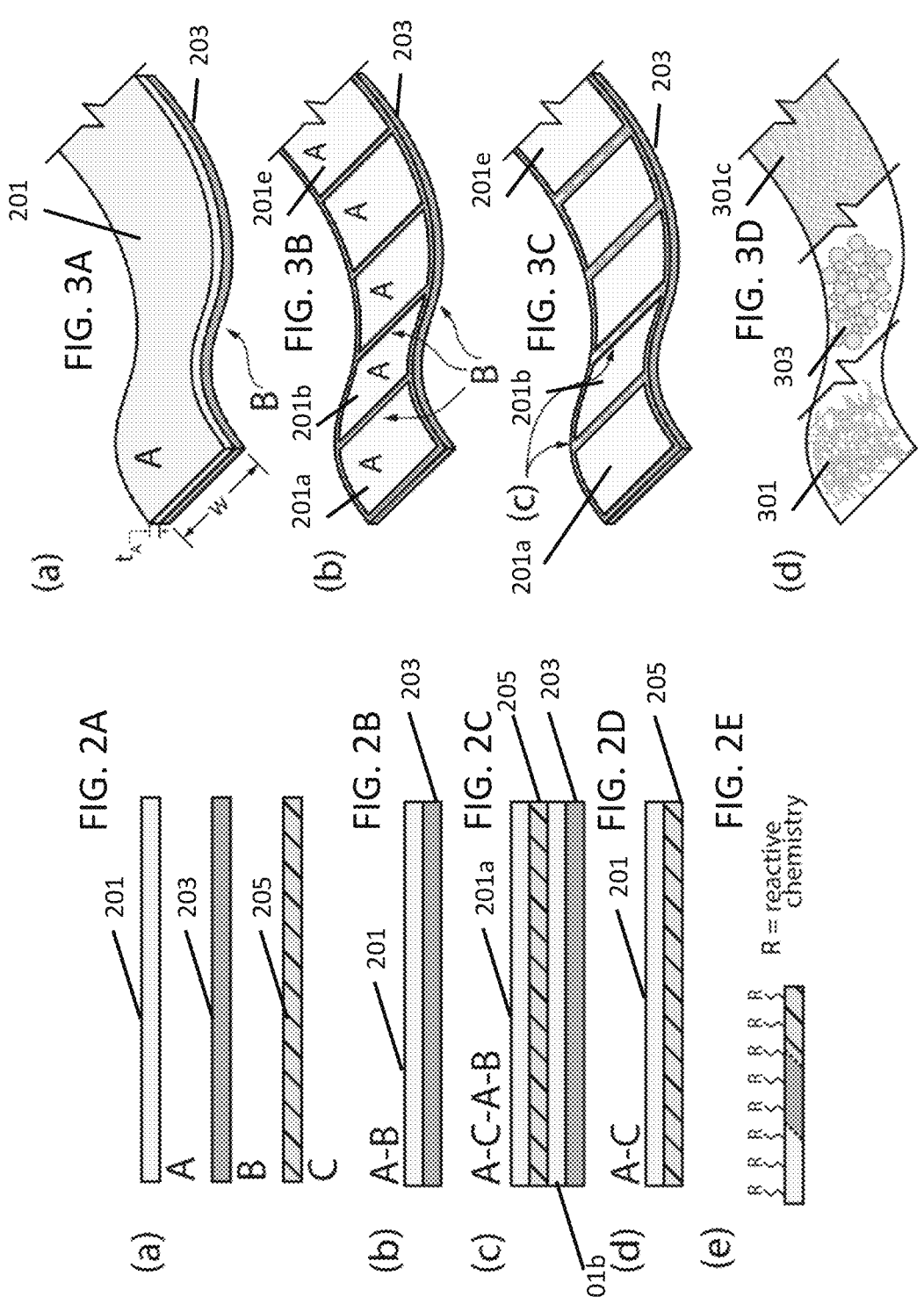

METHODS PROVIDING SAMPLE COLLECTION USING SAMPLE COLLECTION FILMS AND RELATED DEVICES, FILMS, AND REELS

CROSS-REFERENCE TO RELATED APPLICATION

This Application is a Nonprovisional Utility Patent Application and claims the benefit of priority under 35 U.S.C. Sec. 119 based on U.S. Provisional Patent Application No. 63/525,787 filed on Jul. 10, 2023. The disclosure of U.S. Provisional Application No. 63/525,787 and all references cited herein are hereby incorporated in their entirety by reference into the present disclosure.

FEDERALLY SPONSORED RESEARCH AND DEVELOPMENT

The United States Government has ownership rights in this invention. Licensing inquiries may be directed to Office of Technology Transfer, US Naval Research Laboratory, Code 1004, Washington, D.C. 20375, USA; +1.202.767.7230; nrltechtran@us.navy.mil, referencing Navy Case #211163.

TECHNICAL FIELD

The present disclosure relates to methods of collecting samples and related devices and structures.

BACKGROUND OF THE INVENTION

Current methods for time continuous collection of biological samples in a hands-free manner may use expensive infrastructure such as flow assisted cell sorting, and/or potentially complicated systems utilizing custom microfluidic devices.

Flow assisted cell sorting uses a device called a flow cytometer. Briefly, a flow cytometer utilizes a microfluidics chip to direct a stream of dispersed cells or micro tissues from their containing reservoir across a series of lasers to detect and optionally sort tissues based on fluorescence signature. Sorting is completed using an electronic charge of the target and electrostatic deflection plates to direct outgoing streams into collection containers. Use of this technology is pervasive in biology and it could be suited for sample collection, but the devices may be large, expensive, and/or complicated, and/or may require a skilled user to direct the device actively.

Custom microfluidic devices may take many forms. Briefly, these devices may include lithographically formed PDMS (Polydimethylsiloxane) or stacked layers of machined plastics. Flow is driven/pushed through channels by positive pressure or pulled through by suction. Inside chips, channels direct flow via guides, surface phenomena, charge, or directing flows. Use of these technologies are also ubiquitous in the biology space, but such devices are often complicated to design, build, and/or troubleshoot.

Hands-on methods for collection of biological samples may use pipette collection of tissues. Briefly, tissue may be collected via a pipette and placed into a collection container, and requisite solutions may be subsequently added based on desired outcomes. These processes may be time consuming but may offer high levels of customizability and ongoing quality control.

SUMMARY OF THE INVENTION

This summary is intended to introduce in simplified form, a selection of concepts that are further described in the Detailed Description. This summary is not intended to identify key or essential features of the claimed subject matter, nor is it intended to be used as an aid in determining the scope of the claimed subject matter. Instead, it is merely presented as a brief overview of the subject matter described and claimed herein.

According to some embodiments of inventive concepts, a method of collecting liquid samples may include unrolling a portion of a sample collection film from a first reel to a position adjacent a sample dispenser. A liquid sample is dispensed from the sample dispenser onto the portion of the sample collection film. After dispensing the liquid sample onto the portion of the sample collection film, the portion of the sample collection film is rolled onto a second reel.

The sample collection film may include a continuous layer of an absorbent material and a continuous layer of a barrier material. The continuous layer of the absorbent material may be on the continuous layer of the barrier material, and the liquid sample may be dispensed on the continuous layer of the absorbent material.

The sample collection film may include a continuous layer of an absorbent material, the portion of the sample collection film may be a first portion of the sample collection film, and the liquid sample may be a first liquid sample. A second portion of the sample collection film may be unrolled from the first reel to the position adjacent the sample dispenser. After dispensing the first liquid sample, a second liquid sample may be dispensed from the sample dispenser onto the second portion of the sample collection film. After dispensing the second liquid sample, the second portion of the sample collection film may be rolled onto the second reel.

The sample collection film may include a continuous layer of an absorbent material, and unrolling may include sequentially unrolling first and second portions of the sample collection film from the first reel to the position adjacent the sample dispenser. The liquid sample may be continuously dispensed from the sample dispenser onto and between the first and second portions of the sample collection film. Moreover, the first and second portions of the sample collection film may be sequentially rolled onto the second reel.

The sample collection film may include a layer of a barrier material and a plurality of spaced apart frames of absorbent material on the layer of the barrier material. The portion of the sample collection film may include a first frame of the plurality of frames, unrolling the portion of the sample collection film may include unrolling the first frame from the first reel to the position adjacent the sample dispenser, and dispensing may include dispensing a first liquid sample from the sample dispenser onto the first frame of absorbent material. In addition, a second portion of the sample collection film may include a second frame of the plurality of frames of absorbent material. The second frame of absorbent material may be unrolled from the first reel to the position adjacent the sample dispenser. After dispensing the first liquid sample, a second liquid sample may be dispensed from the sample dispenser onto the second frame of absorbent material. After dispensing the second liquid sample onto the second frame of absorbent material, the second portion of the sample collection film may be rolled onto the second reel.

After dispensing the liquid sample onto the portion of the sample collection film, a barrier film may be applied to the portion of the sample collection film. In addition, rolling may include rolling the portion of the sample collection film and the barrier film onto the second reel.

The first reel may include a first spool and a pair of first rims extending from opposite sides of the first spool, and a fresh portion of the sample collection film may be rolled on the first spool between the first rims. The second reel may include a second spool and a pair of second rims extending from opposite sides of the second spool, and an exposed portion of the sample collection film may be rolled on the second spool between the second rims.

Dispensing may include dispensing the liquid sample from at least one of a bioreactor and/or a waste water pipe.

In addition, at least one reagent may be dispensed onto the portion of the sample collection film before and/or after dispending the liquid sample onto the portion of the sample collection film.

At least one reagent may be mixed with the liquid sample before dispensing the liquid sample onto the portion of the sample collection film.

Dispensing may include dispensing the liquid sample from the sample dispenser onto the portion of the sample collection film based on at least one of surface tension, gravity, and/or pumping.

According to some other embodiments of inventive concepts, a sample collection device may include a film dispenser, a film receiver, a driver, and a sample dispenser. The film dispenser is configured to receive a first reel, and a sample collection film is rolled on the first reel. The film receiver is configured to receive a second reel. The driver is coupled with the film receiver, and the driver is configured to turn the second reel to unroll a portion of the sample collection film from the first reel to a dispensing position and then onto the second reel. The sample dispenser is configured to dispense a liquid sample onto the portion of the sample collection film at the dispensing position.

The film dispenser may include a first hub configured to detachably mate with the first reel allowing the first reel to turn when detachably mated with the first hub, and the film receiver may include a second hub configured to detachably mate with the second reel allowing the second reel to turn when detachably mated with the second hub. In addition, the driver may include a motor configured to turn the second reel by turning the second hub when detachably mated with the second reel.

The sample collection film may include a continuous layer of an absorbent material. Moreover, the sample collection film may include a continuous layer of a barrier material with the continuous layer of the absorbent material on the continuous layer of the barrier material, and the sample dispenser may be configured to dispense the liquid sample on the continuous layer of the absorbent material. The portion of the sample collection film may be a first portion of the sample collection film, and the liquid sample may be a first liquid sample.

The driver may be configured to turn the second reel to unroll a second portion of the sample collection film from the first reel to the dispensing position adjacent the sample dispenser. The sample dispenser may be configured to dispense a second liquid sample onto the second portion of the sample collection film after dispensing the first liquid sample. The driver may be configured to turn the second reel to roll the first portion of the sample collection film onto the second reel after the sample dispenser dispenses the first liquid sample and to roll the second portion of the sample collection film onto the second reel after the sample dispenser dispenses the second liquid sample.

The sample collection film may include a continuous layer of an absorbent material. The driver may be configured to sequentially unroll first and second portions of the sample collection film from the first reel to the position adjacent the sample dispenser. The sample dispenser may be configured to continuously dispense the liquid sample from the sample dispenser onto and between the first and second portions of the sample collection film. The driver may be configured to sequentially roll the first and second portions of the sample collection film onto the second reel.

The liquid sample may be a first liquid sample, and the sample collection film may include a layer of a barrier material and a plurality of spaced apart frames of absorbent material on the layer of the barrier material. The portion of the sample collection film may include a first frame of the plurality of frames of absorbent material, and the driver may be configured to unroll the first frame of absorbent material from the first reel to the dispensing position. The sample dispenser may be configured to dispense the first liquid sample onto the first frame of absorbent material.

A second portion of the sample collection film may include a second frame of the plurality of frames of absorbent material, and the driver may be configured to unroll the second frame of absorbent material from the first reel to the dispensing position. The sample dispenser may be configured to dispense a second liquid sample onto the second frame of absorbent material after dispensing the first liquid sample. Moreover, the driver may be configured to roll the second portion of the sample collection film onto the second reel after dispensing the second liquid sample.

The sample collection device may also include a second film dispenser configured to receive a third reel wherein a barrier film is rolled on the third reel, and the driver may be further configured to roll the portion of the sample collection film and a portion of the barrier film onto the second reel.

The first reel may include a first spool and a pair of first rims extending from opposite sides of the first spool, and a fresh portion of the sample collection film may be rolled on the first spool between the first rims. The second reel may include a second spool and a pair of second rims extending from opposite sides of the second spool, and an exposed portion of the sample collection film may be rolled on the second spool between the second rims.

The sample dispenser may be configured to dispense the liquid sample from at least one of a bioreactor and/or a pipe (e.g., a waste water pipe).

In addition, a reagent dispenser may be configured to dispense at least one reagent onto the portion of the sample collection film before and/or after dispensing the liquid sample onto the portion of the sample collection film.

The sample dispenser may be configured to mix at least one reagent with the liquid sample before dispensing the liquid sample onto the portion of the sample collection film.

The sample dispenser may be configured to dispense the liquid sample onto the portion of the sample collection film based on at least one of surface tension, gravity, and/or pumping.

According to still other embodiments of inventive concepts, a sample collection film is configured to capture liquid samples. The sample collection film includes a layer of a barrier material, and a plurality of spaced apart frames of absorbent material on the layer of the barrier material.

A portion of the layer of the barrier material between two of the plurality of frames of absorbent material may include perforations.

The sample collection film may be rolled on a reel. The reel may include a spool and a pair of rims extending from opposite sides of the spool, and the sample collection film may be rolled on the spool between the rims.

According to further embodiments of inventive concepts, a reel includes a spool and a sample collection film. The sample collection film is rolled on the spool, and the sample collection film includes a layer of a barrier material and an absorbent material on the layer of the barrier material.

The layer of the barrier material may be a continuous layer of the barrier material, and the absorbent material may be a continuous layer of the absorbent material on the continuous layer of the barrier material.

The absorbent material may include a plurality of spaced apart frames of the absorbent material on the layer of the barrier material. Moreover, a portion of the layer of the barrier material between two of the plurality of frames of absorbent material may include perforations.

In addition, a pair of rims may extend from opposite sides of the spool, and the sample collection film may be rolled on the spool between the rims.

BRIEF DESCRIPTION OF DRAWINGS

Examples of embodiments of inventive concepts may be more clearly understood from the following detailed description taken in conjunction with the accompanying drawings in which:

FIGS. 1B and 1C are respective side and end views of reels that may be used with sample collection devices of FIG. 1A;

FIG. 1D is a side view of a cassette including a dispensing reel and a storage reel for a sample collection film according to some embodiments of inventive concepts;

FIGS. 2A, 2B, 2C, 2D, and 2E are cross sectional views of materials and structures that may be used for sample collection films of FIG. 1A according to some embodiments of inventive concepts;

FIGS. 3A, 3B, 3C, and 3D are plan views of sample collection films based on materials and structures of FIGS. 2A, 2B, 2C, 2D, and 2E according to some embodiments of inventive concepts;

DETAILED DESCRIPTION OF THE INVENTION

Figure 1A:
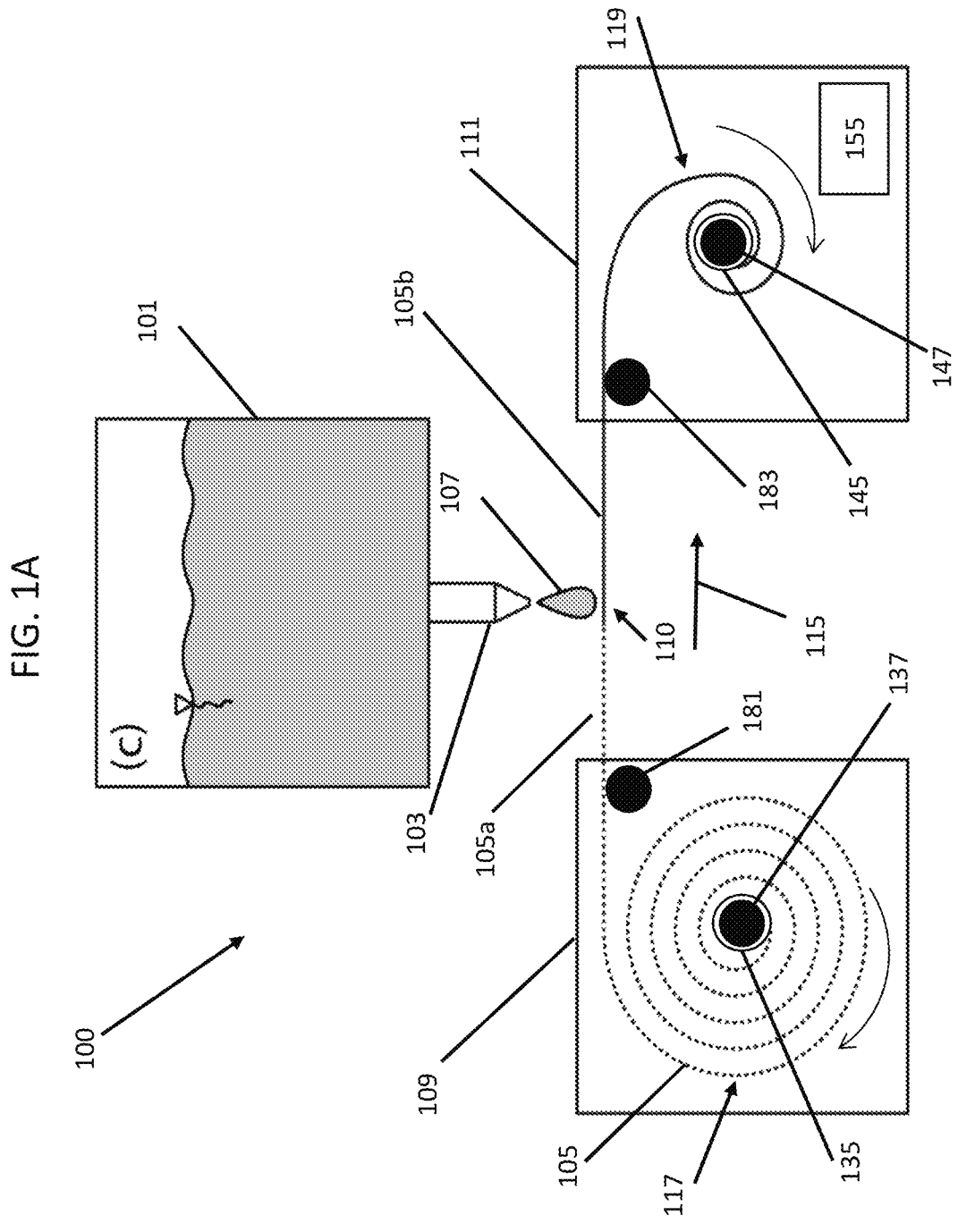
FIG. 1A is a diagram illustrating sample collection devices according to some embodiments of inventive concepts.

Aspects and features of the present disclosure will now be described more fully with reference to the accompanying drawings. The following description shows, by way of example, combinations and configurations in which aspects, features, and embodiments of inventive concepts can be put into practice. It will be understood that the disclosed aspects, features, and/or embodiments are merely examples, and that one skilled in the art may use other aspects, features, and/or embodiments or make functional and/or structural modifications without departing from the scope of the present disclosure. Moreover, like reference numerals refer to like elements throughout, and sizes of each of the elements may be exaggerated for clarity and conveniences of explanation.

Some embodiments of present inventive concepts may provide a device that collects biological samples and/or suspension particulates continuously over time or at discrete times in a hands-free/automated manner while simultaneously storing samples in a stable, accessible, and/or customizable matrix for future processing/testing. Traditionally, this type of sample collection has been done using hands-on approaches such as pipetting or material transfer across time. However, manual techniques may be unsuitable for future endeavors related to quarantined operations in low earth orbit which may demand hands-free/automated systems given regulatory policies related to biosafety levels beyond BSL1 (Bio-Safety Level 1). Embodiments of inventive concepts may be applied for terrestrial use, extraterrestrial/space/orbital use, and/or commercial use. Such embodiments may enable sample collection and/or bio-sensing in austere environments, and/or passive solid-state bio-recording for downstream assay preparation and/or historical sample storage.

According to some embodiments of inventive concepts, a liquid may be captured by unrolling a sample collection film including an absorbent material to which samples of the liquid (liquid samples) are applied over time, and rerolling the sample collection film to store the samples.

A sample collection device 100 according to some embodiments of inventive concepts is shown in the diagram of FIG. 1A. Sample collection device 100 may include a sample dispenser 103 (e.g., a nozzle dispensing by extrusion, pumping, surface tension, gravity, etc.) coupled with a sample source (e.g., a bioreactor 101 that generates a biological liquid/solution/suspension of interest), a sample collection film 105 (also referred to as a sample collection tape, tape, or film) configured to capture a dispensed liquid sample 107 (e.g., a biological liquid sample from the sample source), a film dispenser 109 configured to detachably receive a dispensing reel 117 including fresh/unexposed film 105a, and a film receiver 111 configured to detachably receive a storage reel 119 used to store exposed film 105b with liquid samples 107 thereon.

In FIG. 1A, sample dispenser 103 (e.g., including a nozzle) dispenses a liquid sample (e.g., a drop of the liquid) 107 from a source (e.g., a bioreactor 101) onto sample collection film 105, where the liquid sample 107 may contain a biological material and/or a kinetically reacting material. More particularly, the liquid sample 107 is dispensed onto sample collection film 105 that is unrolled from dispensing reel 117 in film dispenser 109 and that is then rolled back up on storage reel 119 in film receiver 111. Accordingly, fresh sample collection film 105a is dispensed (e.g., unrolled) from dispensing reel 117 by film dispenser 109 to dispensing position 110 (also referred to as a sampling position) adjacent sample dispenser 103 in the direction of arrow 115 as liquid samples 107 are applied to fresh sample collection film 105a at dispensing position 110, and exposed sample collection film 105b is stored (e.g., rolled) on storage reel 119 in film receiver 111.

As shown in FIG. 1A, liquid samples 107 (e.g., drops) from the source (e.g., bioreactor 101) are provided through sample dispenser 103 (e.g., extruded) as sample collection film 105 is unrolled from film dispenser 109 to advance in direction 115 so that each sample 107 is collected on previously unexposed film 105*a*, and exposed film 105*b* is rolled on storage reel 119 for storage on storage reel 119 in film receiver 111. According to some embodiments, gravity, surface tension, and/or pumping may drive liquid samples 107 from a nozzle of sample dispenser 103 onto sample collection film 105. In some embodiments, fresh sample collection film 105*a* may be provided as a roll on dispensing reel 117, and fresh sample collection film 105*a* may be dispensed by unrolling from the dispensing reel 117 in film dispenser 109. Similarly, exposed film 105*b* may be received by film receiver 111 and rolled onto a storage reel 119. In FIG. 1A, the dashed line represents unexposed/fresh sample collection film 105*a* (also referred to as unexposed/fresh film), and the solid line represents exposed sample collection film 105*b* that has been exposed to liquid samples 107 (also referred to as exposed film).

According to some embodiments, film dispenser 109 and film receiver 111 may be provided separately, and according to some other embodiments, film dispenser 109 and film receiver 111 may be integrated. In addition, rollers 181 and 183 may be provided to maintain the film 105 at the dispensing position as a thickness of fresh film on reel 117 is reduced due to unrolling and as a thickness of exposed film on reel 119 increases due to rolling.

According to some embodiments, dispensing reel 117 may include fresh sample collection film 105 rolled on spool 135, and spool 135 may be configured to detachably mate with hub 137 of film dispenser 109. Moreover, hub 137 may be configured to turn while detachably mated with dispensing reel 117, thereby allowing sample collection film 105 to unroll/dispense past sample dispenser 103. Accordingly, a new dispensing reel 117 with fresh sample collection film 105 may be attached to hub 137, and then the empty dispensing reel 117 may be removed from hub 137 after use. In addition, dispensing reel 117 may include first and second rims extending from opposite sides of spool 135 with fresh sample collection film 105 rolled on spool 135 between the rims.

Similarly, storage reel 119 may include spool 145 that is configured to detachably mate with hub 147 of film receiver 111. In addition, storage reel 119 may include first and second rims extending from opposite sides of spool 145, so that exposed film is rolled onto spool 145 between the rims of storage reel 119. In addition, driver 155 may be coupled with hub 147, and driver 155 may be configured to turn hub 147 and storage reel 119 to roll exposed sample collection film 105*b* onto storage reel 119. Driver 155, for example, may include an electric motor configured to turn hub 146 (e.g., directly, via gear, via belt, etc.). Moreover, torque may be transferred between hub 147 and reel 119 via friction, grooves, teeth, etc.

Once all of the sample collection film 105 has been used, the sample collection film may be disconnected from dispensing reel 117 and rolled onto storage reel 119, and storage reel 119 (with the exposed sample collection film 105*b* rolled thereon) may be removed from film receiver 111 (e.g., detached from hub 147) for storage and/or analysis. According to some other embodiments, once all of the sample collection film 105 has been used, an additional driver in film dispenser 109 may be used roll the exposed sample collection film back onto the dispensing reel for storage and/or analysis.

According to some embodiments, dispensing reel 117 and storage reel 119 may be provided separately so that unexposed/fresh sample collection film 105 on a new dispensing reel 117 is separate from any storage reel 119. In such embodiments, the new dispensing reel 117 may be provided in film dispenser 105 (e.g., with spool 135 detachably mated with hub 137), empty storage reel 119 may be provided in film receiver 111 (e.g., with spool 145 detachably mated with hub 147), and a leader of the new sample collection film 105 may be fed from the new dispensing reel 117 and connected to the spool 145 of the empty storage reel 119 in film receiver 111. Sample collection film 105 can thus be advanced from dispensing reel 117 past sample dispenser 103 and onto storage reel 119 to collect and store discrete samples 107 until all usable sample collection film 105 from dispensing reel 117 has been used.

Once all usable sample collection film has been used, any remaining sample collection film 105 may be disconnected from dispensing reel 117 and rolled onto storage reel 119, and storage reel 119 can be removed for storage and/or analysis of the samples collected on exposed film 105*b*. In an alternative, once all usable film has been used, exposed film 105*b* can be rolled from storage reel 119 back onto dispensing reel 117 (in a rewind operation) and disconnected from storage reel 119, and dispensing reel 117 can be removed for analysis of the samples collected on exposed film 105*b*. Film receiver 111 may include driver 155 coupled with storage reel 119 via hub 147 and configured to turn storage reel 119 to pull film 105 from dispensing reel 117 onto storage reel 119. If the exposed film is to be rolled back onto dispensing reel 117, film dispenser 109 may also include a rewind driver coupled with dispensing reel 117 via hub 137 and configured to turn dispensing reel 117 to pull the exposed film 105*b* from storage reel 119 back onto dispensing reel 117. In such embodiments, dispensing reel 117 and/or storage reel 119 may be respectively removable from film dispenser 109 and/or film receiver 111 to allow insertion/use of new/fresh reels/film.

A reel 173 according to some embodiments of inventive concepts is illustrated in side and end views of FIGS. 1B and 1C. The structure of reel 173 illustrated in FIGS. 1B and 1C may be used to implement dispensing reel 117 or storage reel 119 of FIG. 1A. As shown, reel 173 may include cylindrical spool 175 and circular rims 177 extending from opposite sides of spool 175. Moreover, opening 179 through spool 175 may be configured to detachably mate with hub 137 or 147 of FIG. 1A. When used to implement dispensing reel 117 of FIG. 1A, a roll of fresh sample collection film 105*a* may be provided around spool 175 between rims 177, opening 179 may be detachably mated to hub 137 of film dispenser 109, and fresh sample collection film 105*a* may be unrolled from the reel (so that spool 135 of FIG. 1A is provided by spool 175). When used to implement storage reel 119, opening 179 may be detachably mated to hub 147 of film receiver 111, and exposed sample collection film 105*b* may be rolled onto spool 175 between rims 177 (so that spool 145 of FIG. 1A is provided by spool 175). Moreover, rims 177 may be omitted for either dispensing reel 117 and/or storage reel 119.

Cylindrical opening 179 of reel 173 may be configured to slide over a respective hub 137/147 to detachably mate therewith. The detachable mating, for example, may be provided via friction, a snap/spring fitting, a lock, etc. Moreover, torque from a driven hub (e.g., turning responsive to driver 155 and hub 147) may be applied to a respective reel via friction between spool opening 179 and the respective hub, via teeth/grooves in hub and/or spool opening 179, etc.

According to some other embodiments, dispensing reel 117 and storage reel 119 may be integrated in a cassette as shown in FIG. 1D. In a cassette, dispensing and storage reels 117 and 119 may be provided in a cassette shell 191, and an opening 193 in the cassette shell 191 may expose film 105 to liquid samples 107 at dispensing position 110 as sample collection film 105 advances from dispensing reel 117 to storage reel 119. Moreover, rollers 181 and 183 may maintain alignment of film 105 with opening 193 and dispensing position 110. With a cassette, film dispenser 109 and film receiver 111 may be integrated in a film feeder that is configured to accept the cassette to mate driver 155 with spool 145 of storage reel 119 (via hub 147), and to turn storage reel 119 to pull film 105 from dispensing reel 117 onto storage reel 119. Such a film feeder may also include a driver configured to couple with spool 135 of dispensing reel 117 (via hub 137) to rewind the film back onto the dispensing reel 117 for storage and/or analysis after collecting samples. Accordingly, openings in sides of shell 191 may be aligned with holes in spools 135 and 145 to allow coupling between respective spools 135/145 and hubs 137 and 147. With a cassette, both dispensing and storage reels may be permanently housed in shell 191 thereby: reducing handling of film 105 and reels 117 and 119; protecting unexposed/fresh film 105 before use; and protecting exposed film and collected samples after use.

Various structures of sample collection film 105 are illustrated in cross section in FIGS. 2A-2E. As shown in FIG. 2A, sample collection film 105 may include one or more of an absorbent material 201 indicated with light shading (e.g., an absorbent 3D material), a barrier material 203 indicated with dark shading, and/or a porous membrane material 205 indicated with cross-hatch (e.g., a nano/micro porous membrane material). According to some embodiments, absorbent material 201 may include a three dimensional (3D) absorbent material. Absorbent material 201, for example, may include one or more of a cellulose paper, a filter paper, a glass fiber sheet, chromatography paper, a flexible sintered micro-particle sheet, and/or a generally hydrophilic fiber sheet. Barrier material 203, for example, may include one or more of an impermeable material such as sticky tape, a polymeric film/layer, a printable wax, and/or a coating that is hydrophobic with respect to absorbent material 201. Porous membrane material 205, for example, may include one or more of a polymeric porous membrane and/or a compressed absorbent material.

As shown in the cross section of FIG. 2B and in the plan view of FIG. 3A, sample collection film 105 (having width W) may include a continuous layer of absorbent material 201 (having thickness ta) on a continuous layer of barrier material 203 (e.g., an impermeable barrier material) according to some embodiments. Accordingly, absorbent material 201 may absorb liquid samples 107, and film 105 may then be rolled onto storage reel 119 of film receiver 111 so that different layers of the exposed absorbent material 201 in the roll are separated by the continuous layer of barrier material 203. Accordingly, cross contamination and/or interaction between different layers of exposed absorbent material 201 in the roll can be reduced/avoided.

As shown in FIG. 2C, sample collection film 105 may include a layer of porous membrane material 205 sandwiched between two layers of absorbent material 201a and 201b on a layer of barrier material 203. Accordingly, excess liquid from a sample 107 provided on the first layer of absorbent material 201a may be extracted through porous membrane layer 205 into the second layer of absorbent material 201b leaving behind particulates in/on first layer of absorbent material 201a. As with the structure of FIG. 2B, the layer of barrier material 205 may reduce/avoid cross contamination and/or interaction between samples on different layers of exposed film when rolled in film receiver 111.

As shown in FIG. 2D, sample collection film 105 may include a layer of absorbent material 201 on porous membrane layer 205. In FIG. 2D, excess liquid from a liquid sample may be extracted through porous membrane 205 leaving behind particulates in/on absorbent material 201, and a layer of an impermeable barrier material (also referred to as a counter material/layer) may be added to the film after sample exposure and before rolling in film receiver 111 to reduce/prevent cross contamination and/or interaction between different layers of the exposed film in the roll on storage reel 119.

As shown in FIG. 2E, film 205 may include a single layer with different sections of absorbent material 201, impermeable barrier material 205, and/or porous membrane material 205. In embodiments of FIG. 2E, all materials could be functionalized via surface engineering techniques such as silanization, thiolization, carboxylation, etc. Functionalization techniques could be implemented, for example, to alter surface energy, to facilitate catalysis and/or to facilitate biomolecule capture and/or particulate retention.

One side of the film 105 may include a layer of a non-reactive impermeable barrier material 203 and a layer of an absorbent material 201 as discussed above with respect to FIGS. 2B and 3A. The layer of the barrier material may reduce/avoid cross contamination of liquid samples across rolled layers of exposed film 105b on storage reel 119. The absorbent material 201 may include one or more of fibrous glass, sintered glass particles, sintered polymeric particles, synthetic fibers, biomaterial fibers, and/or other natural absorbent materials. An extrusion rate of liquid sample(s) 107 through sample dispenser 103 and roll size (e.g., width of film, thickness of film, thickness of absorbent material 201, and/or length of film) and traveling speed of film 105 can be calibrated to a rate of biological production and capture equilibrium and/or toward a timed depletion of the bioreactor 101.

FIG. 3A illustrates a plan view of a portion of sample collection film 105 that may include a continuous layer of absorbent material 201 on a continuous layer of an impermeable barrier material 203, and a thickness ta and width W can be customized based on application (e.g., to adjust volumetric capacity requirements). The sample collection film of FIG. 3A can thus be used for time continuous absorbance of liquid sample 107 as sample collection film 105 advances from dispenser reel to storage reel. With storage collection film 105 having a continuous layer of absorbent material 201, a steady feed of storage collection film 105 past sample dispenser 103 can be used to collect a continuous stream of liquid sample 107 or a series of sample drops over time.

FIG. 3B illustrates a plan view of a portion of sample collection film 105 that may include discrete layers of absorbent material (also referred to as frames of absorbent material, absorbent frames, or just frames) 201a, 201b, etc. provided on a continuous layer of an impermeable barrier material 203, and adjacent frames 201a, 201b, etc. may be separated by impermeable barriers (labeled "B" in FIG. 3B) or just spaced apart on the layer of the barrier material 203. Each frame 201a, 201b, etc. is thus separated from adjacent frames to reduce/avoid cross contamination between discrete samples 107 collected in respective discrete layers/ frames of absorbent material. Stated in other words, discrete samples 107 (e.g., drops) can be collected on respective discrete layers/frames of absorbent material at discrete intervals of time, and a frame identifier may be provided on the film 105 for each discrete frame to facilitate identification of a time at which a respective sample was taken. Accordingly, the frame identifiers may relate to the time domain. More particularly, film receiver 111 may drive reel 119 to advance sample collection film 105 so that each liquid sample 107 is received by a respective frame 201*a*, 201*b*, etc. of film 105.

FIG. 3C illustrates a plan view of a portion of sample collection film 105 that may include discrete frames 201*a*, 201*b*, etc. separated by impermeable barriers on a layer of an impermeable barrier material 203 as discussed above with respect to FIG. 2B. In addition, sample collection film 105 of FIG. 3C may include perforations between absorbent frames to facilitate separation of discrete frames and/or sections of discrete frames for analysis. For example, perforations may be provided through the centers of respective impermeable barriers and/or the continuous layer of the barrier material 203 between frames so that portions of impermeable barriers remain at each end of a discrete frame after separation of adjacent frames along perforations. Such perforations may allow a user deliberate selection of individual frames or time sets of frames for analysis, and each frame may include an identifier (e.g., an alpha/numeric identifier, a bar/QR code, etc.) that may be used to identify a time that a sample of the layer/frame was taken.

As shown in the plan view of FIG. 3D, sample collection film 105 may include continuous and/or discrete layers of absorbent material formed from a variety of 3D materials including one or more of fibrous materials 301, microparticles 303 adhered and/or sintered to a 2 dimensional (2D) surface of a layer of an impermeable barrier material, and/or a lithographically formed and/or machined surface 305 formed on a layer of an impermeable barrier material. According to some embodiments, the continuous layer of absorbent material 201 of FIG. 3A may be formed using a single one of the materials of FIG. 3D, or different materials of FIG. 3D may be used for different segments of the continuous layer of absorbent material 201 of FIG. 3A. According to some embodiments, each discrete frame of FIGS. 3B and 3C may be formed of a same one of the materials of FIG. 3D, or adjacent ones of the discrete frames may be formed of different ones of the materials of FIG. 3D so that different samples may be collected close in time using different ones of the materials of FIG. 3D.

The plan views of FIGS. 3A-D thus illustrate short segments of different structures that may be used to implement sample collection film 105. Accordingly, actual sample collection films implemented using one or more structures of FIGS. 3A-D may have lengths much greater than that illustrated in FIGS. 3A-D. Moreover, any of the sample collection films of FIGS. 2A-E and/or 3A-E may be rolled onto a reel 173 as shown in FIGS. 1B-C to provide a reel of fresh/unexposed sample collection film 105. Moreover, a reel of fresh/unexposed sample collection film may be detachably mated with hub 137 to provide dispensing reel 117, and an exposed end of the fresh/unexposed sample collection film 105 may be unrolled and connected to spool 145 of a storage reel 119 that is detachably mated with hub 147. The fresh/unexposed sample collection film 105 may thus be unrolled from dispensing reel 117 and rolled onto storage reel 119 while liquid samples 107 from sample dispenser 103 are applied to different portions of sample collection film 105 over time as discussed above with respect to FIG. 1A. Once all of the fresh sample collection film has been used, any remaining film may be detached from spool 135 of dispensing reel 117 and rolled onto storage reel 119, and the storage reel 119 may be removed from hub 147 for storage and/or analysis of the collected samples. Moreover, the empty dispensing reel 117 may be removed from hub 137 and replaced with a new reel of fresh sample collection film.

As discussed above with respect to FIGS. 1A and 3A, sample collection device 100 may be used with a sample collection film 105 including a continuous layer of absorbent material 201 on a continuous layer of barrier material 203. In such embodiments, sample dispenser 103 may be configured to dispense discrete samples that are spaced apart on the absorbent material as sample collection film 105 advances in direction 115 over time, or sample dispenser 103 may be configured to dispense samples as a continuous flow on the absorbent material as sample collection film 105 advances in direction 115.

When dispensed as discrete samples, driver 155 is configured to turn storage reel 119 to unroll portions of sample collection film 105 from dispensing reel 117 to dispensing position 110 adjacent sample dispenser 103. As each portion of sample collection film 105 is advanced to dispensing position 110, sample dispenser 103 is configured to dispense a discrete sample 107 onto the respective portion of sample collection film 105 so that each discrete sample 107 is spaced apart from other discrete samples on the film 105. In particular, driver 155 is configured to advance sample storage film 105 a sufficient distance between dispensing of consecutive samples so that each sample captured on the absorbent material of the sample collection film is separate and spaced apart from adjacent samples.

When dispensed as a continuous flow, driver 155 is configured to turn storage reel 119 to unroll portions of sample collection film 105 from dispensing reel 117 to dispensing position 110 adjacent sample dispenser. As the sample collection film 105 is advanced past dispensing position 110, sample dispenser 103 is configured to continuously dispense the liquid sample onto the absorbent material.

As discussed above with respect to FIGS. 1A and 3B, sample collection device 100 may be used with a sample collection film 105 including a barrier layer and a plurality of spaced apart frames of absorbent material on the barrier layer. Driver 155 is configured to turn storage reel 119 to unroll portions of sample collection film 105 from dispensing reel 117 so that the frames of absorbent material are separately advance to dispensing position 110. As each frame is advanced to dispensing position 110, sample dispenser 103 is configured to dispense a respective discrete sample 107 onto the respective frame.

Figure 6:
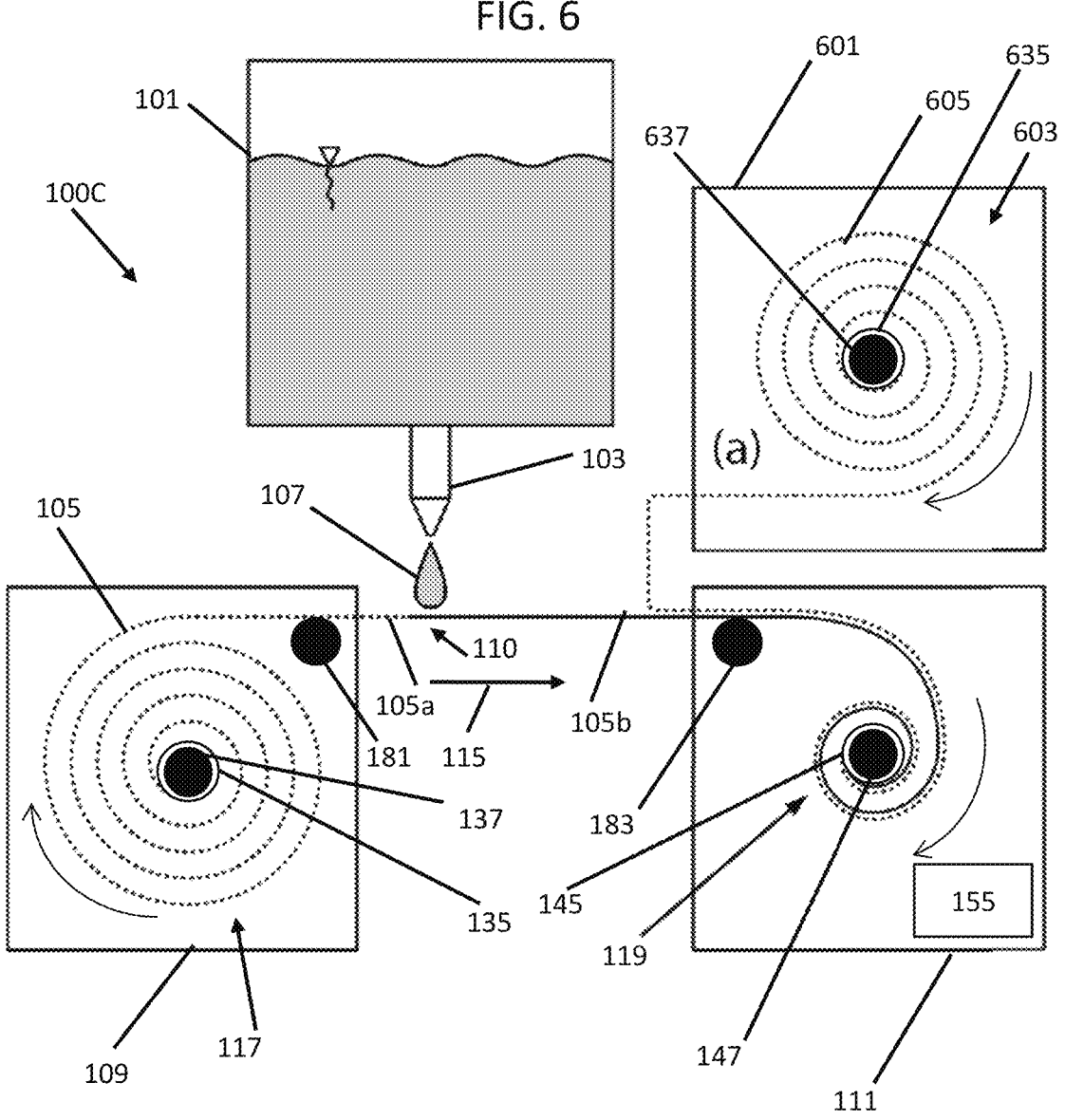
Figure 7:
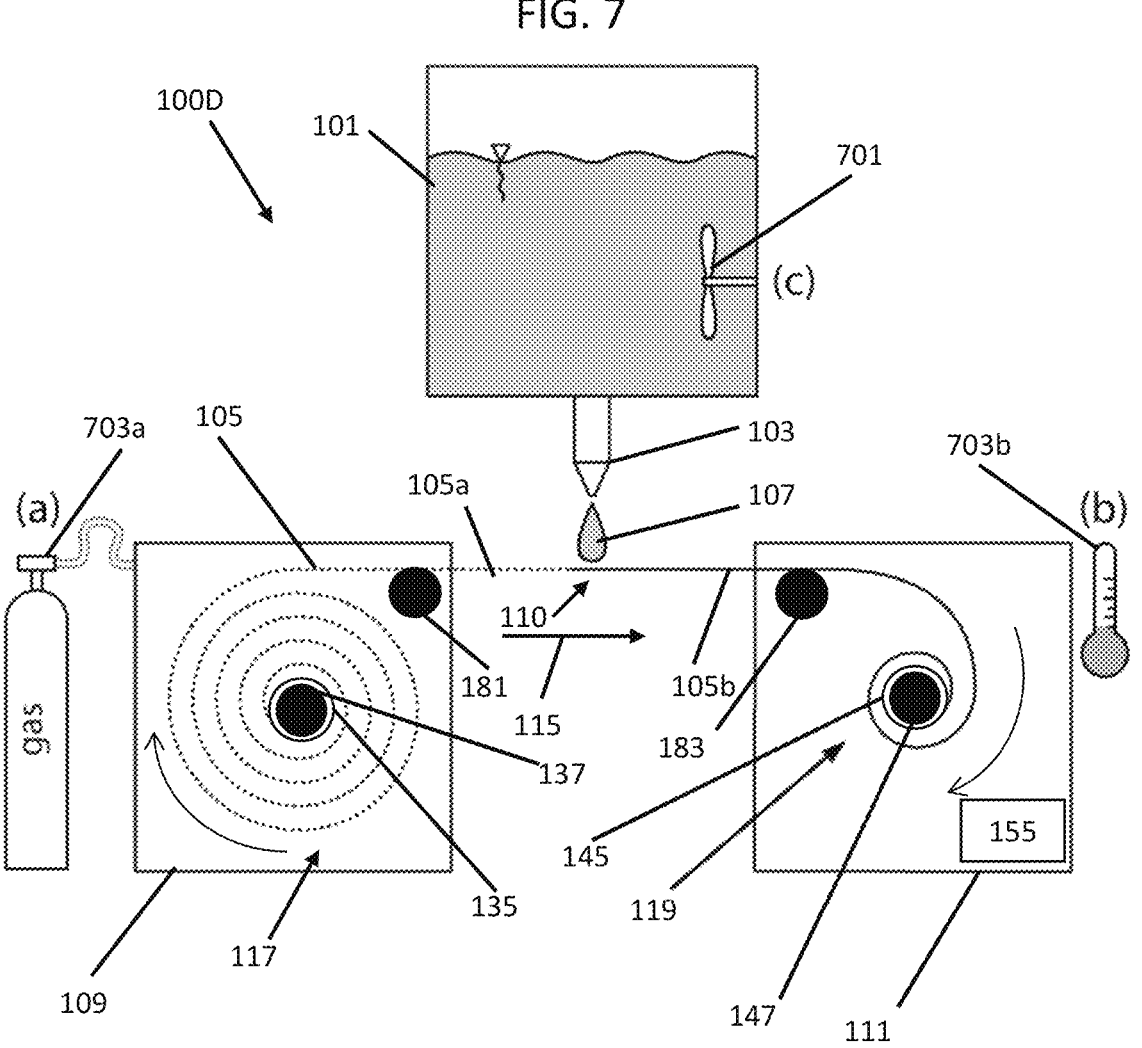

Components of the sample collection device 100, and operations thereof can be expanded to suit a user's needs such as: compartmentalization of sections of the absorbent/fibrous portions of film 105 for time-discrete capture of biological material (as discussed with respect to FIGS. 3B and 3C); customization of layers of the absorbent material and/or barrier material via perforation for subsequent selective removal (as discussed with respect to FIG. 3C); functionalization of the absorbent material to capture biomolecules or tissues (as discussed with respect to FIGS. 2A-2E); addition of secondary dispensers and/or reservoirs for upstream preparation and/or downstream mixing of biological material with reagents (as discussed with respect to FIGS. 4 and 5); secondary juxtaposing fibrous or non-fibrous layers/sheets as barriers or distinct functionalization surfaces (as discussed with respect to FIG. 6); bioreactor additions provided to enhance mixing such as agitators (as discussed with respect to FIG. 7); thermal elements (e.g., heating and/or cooling elements) to heat and/or cool biological material storage of infilled porous sheets to maintain biomolecule stability (as discussed with respect to FIG. 7); and/or storage containers of porous sheets, both unfilled and filled, for reactivity maintenance and biological compound stability, respectively (as discussed with respect to FIG. 7).

Figure 4:
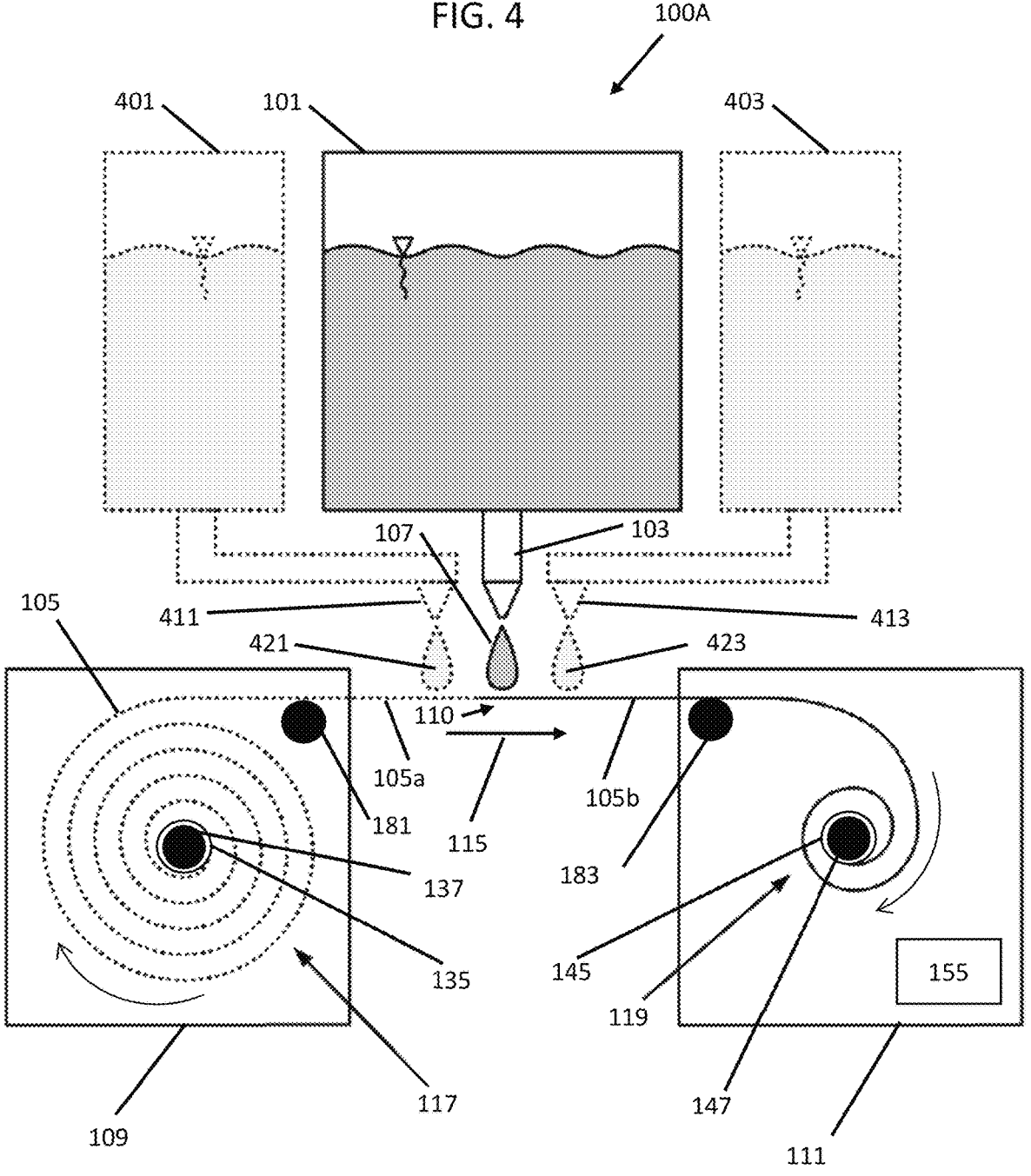
FIGS. 4, 5, 6, and 7 are diagrams illustrating sample collection devices according to some embodiments of inventive concepts.

FIG. 4 illustrates sample collection device 100A according to some additional embodiments of inventive concepts including all elements discussed above with respect to FIG. 1 and including additional reagent reservoirs 401 and 403 and respective reagent dispensers 411 and 413. In FIG. 4, upstream reagent dispenser 411 and/or downstream reagent dispenser 413 may be used to add reagents to an absorbent surface of sample collection film 105 before and/or after dispensing liquid sample 107. One or more reagents may be added to perform one or more functions, or combinations of functions, including but not limited to surface functionalization, preparation of functionalized surfaces, reaction with main reactor constituents of sample 107, preservation of constituents of sample 107, and/or performance of secondary reactions with constituents of sample 107 against functional surfaces.

When using sample collection film 105 with a continuous layer of absorbent material (e.g., as discussed with respect to FIGS. 2B and 3A) with sample collection device 100A of FIG. 4, sample dispenser 103 may continuously dispense sample 107 from bioreactor 101 onto sample collection film 105 while reagent dispensers 411 and 413 dispense respective reagents 421 and 423 from reagent reservoirs 401 and 403 onto sample collection film 105. While one reagent dispenser 411 is shown dispensing reagent 421 from reagent reservoir 401 on sample collection film 105 upstream from sample dispenser 103, multiple reagent dispensers for multiple reagent reservoirs may be provided upstream from sample dispenser 103. Similarly, while one reagent dispenser 413 is shown dispensing reagent 423 from reagent reservoir 403 on sample collection film 105 downstream from sample dispenser 103, multiple reagent dispensers for multiple reagent reservoirs may be provided downstream from sample dispenser 103. Moreover, embodiments of FIG. 4 may be provided without any upstream reagent dispensers/reservoirs, or embodiments of FIG. 4 may be provided without any downstream reagent dispensers/reservoirs.

When using sample collection film 105 with separate/discrete frames of absorbent material 201a, 201b, etc. as discussed with respect to FIGS. 3B and 3C with sample collection device 100A of FIG. 4, each discrete frame of absorbent material will sequentially pass reagent dispenser 411, sample dispenser 103, and reagent dispenser 413. Accordingly, each discrete frame of absorbent material may first receive reagent 421 from reagent reservoir 401 via reagent dispenser 411, followed by receiving sample 103 from bioreactor 101 via sample dispenser 103, and then followed by receiving reagent 423 from reagent reservoir 401 via reagent dispenser 413. Reagent 421 may be used to prepare a surface of sample collection film 105 to receive sample 107 and/or react with biological material of sample 107, and/or reagent 423 may be used to react with biological material of sample 107. Examples of reagents may include cell lysing fluids such as TritonX and/or buffering solutions.

Figure 5:
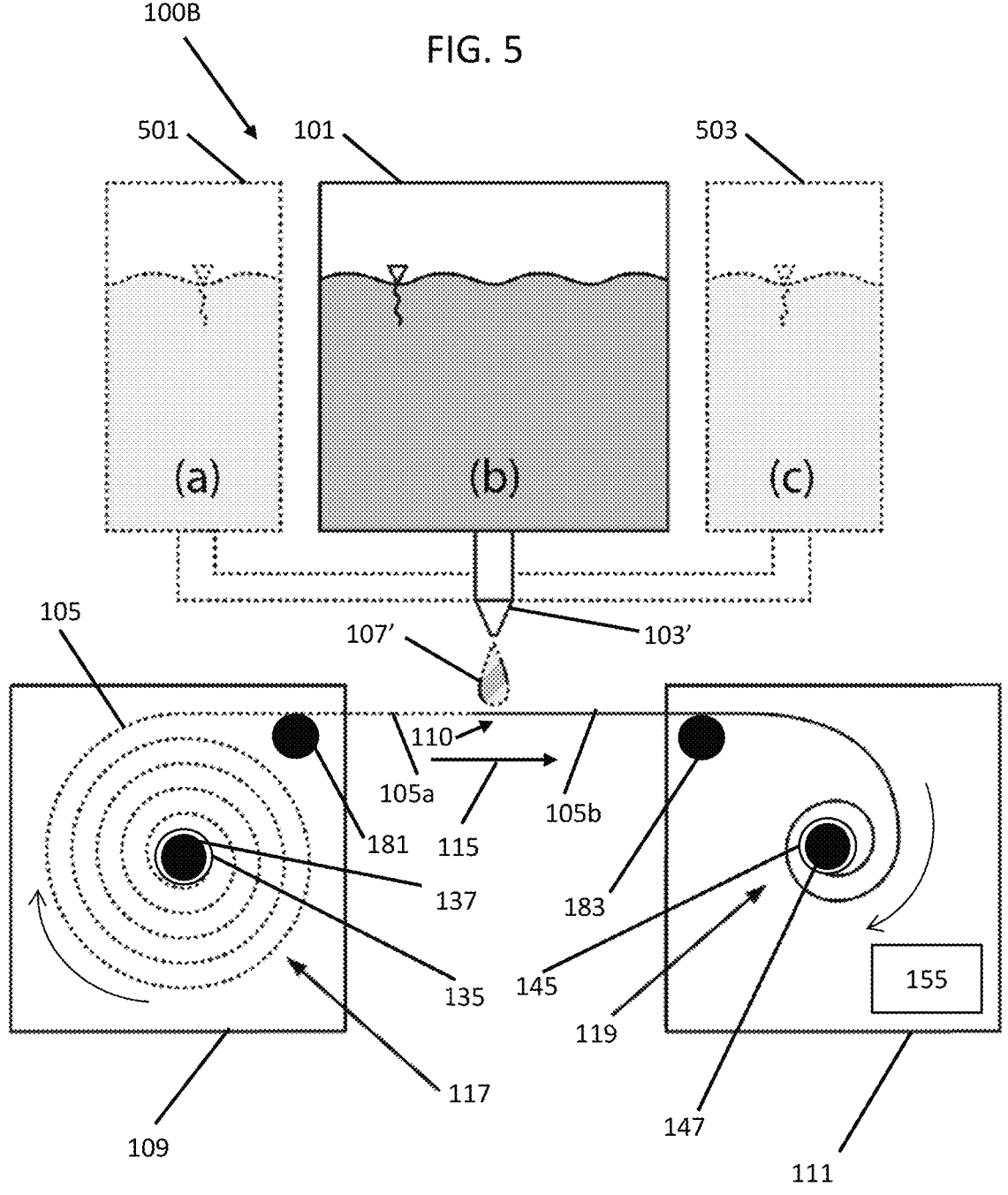

FIG. 5 illustrates sample collection device 100B according to some additional embodiments of inventive concepts including all elements discussed above with respect to FIG. 1 and including additional reagent reservoirs 401 and 403. In FIG. 5, sample dispenser 103' may be configured to include in-flow addition of one or more reagents to the sample material of bioreactor 101 in a predetermined order to provide in-flow mixing of biological material with reagents for in situ chemical processing before dispensing as sample 107'. For example, sample dispenser 103' may be configured to first mix reagent (a) of reagent reservoir 501 and sample material of bioreactor 101 before mixing with reagent (c) of reagent reservoir 503 and dispensing the sample 107'. Mixing or addition order may be related to microfluidic needs of the dispenser head if these needs exist or in-flow chemical process necessities. While FIG. 5 illustrates 2 reagent reactors, embodiments of FIG. 5 may be implemented with only one reagent reactor adding only one reagent to the sample material to provide sample 107', or with 3 or more reagent reactors adding 3 or more reagents to the sample material to provide sample 107'. Such mixing, for example, may provide cellular encapsulation before deposition onto sample collection film 105 for cell preservation and/or segregation.

According to still other embodiments of inventive concepts, elements of FIGS. 4 and 5 may be combined. For example, at least one reagent reservoir may provide at least a first reagent that is mixed by sample dispenser 103' with the sample material from bioreactor 101 to provide sample 107', and at least one reagent reservoir may provide at least a second reagent that is separately dispensed on sample collection film 105 upstream and/or downstream of sample 107'.

FIG. 6 illustrates sample collection device 100C according to some additional embodiments of inventive concepts including all elements discussed above with respect to FIG. 1 and including second film dispenser 601 configured to dispense barrier film 605 from reel 603 including spool 635 that is detachably mated with hub 637. In FIG. 6, for example, sample collection film 105 may be provided as discussed with respect to any of FIGS. 2B, 2C, 2D, 2E, 3A, 3B, 3C, and/or 3D. In FIG. 6, barrier film 605 may be applied to a surface of sample collection film 105 downstream from sample dispenser 103. Surfaces of sample collection film 105 may be formed from previously described layers 201 (A) and/or 203 (B) from FIG. 2A, including a combination of surface layers 201 (A) and/or 203 (B), or being distinctly different from surface layers 201 (A) or 203 (B). Functionalization of sample collection film targeting different surface phenomena than surface layer 201 (A) or surface layer 203 (B) may also be possible.

According to some embodiments of FIG. 6, sample collection film 105 may be provided as discussed above with respect to FIG. 2D with a continuous layer of absorbent material 201 but without a layer of an impermeable barrier material, and barrier film 605 may include a layer of an impermeable barrier material that is provided on the absorbent material 201 of sample collection film 105 downstream from dispensing samples 107 and upstream from rolling on storage reel 119. Accordingly, barrier film 605 may provide a layer of an impermeable barrier material between different layers of sample collection film 105 when rolled onto storage reel 603. According to some other embodiments, sample collection film 105 may include an absorbent material 201 on a layer of an impermeable barrier material 203, and barrier film 605 may include a layer of an impermeable barrier material so that absorbent material 201 is sandwiched between two layers of impermeable barrier material when rolled onto storage reel 119. Sample collection film 105 and barrier film 605 may be formed from layer type combinations or bioconjugated differently to perform simultaneous operations.

FIG. 7 illustrates sample collection device 100D according to some additional embodiments of inventive concepts including all elements discussed above with respect to FIG. 1 and including reactor mixing device 701 and environmental controls 703a and 703b. Film storage may be altered using one or more inert gas sources 793a and/or temperature control source 703b or both to provide stability and/or reactivity of film surfaces, liquid constituents, and/or biological material therein. For example, fresh film 105a at film dispenser 109 and/or exposed film 105b at film receiver 111 may be stored in an inert gas environment using inert gas source 703a and/or heated/cooled using temperature control system 703b. In addition, aeration may be provided for the material in bioreactor 101.

According to some embodiments of the present disclosure, a low component sample collection device may provide time continuous or discrete time collection of biological material for subsequent analysis and/or processing. Some embodiments may provide a hands-free low infrastructure framework to collect such biological material, design simplicity, customizability of collection via material selection or functionalization, and/or customizability of functional complexity via upstream, downstream, and/or in-flow reagent addition.

Bioreactor 101 may be provided using dispenser 103 (e.g., a dispensing needle) to provide a perfusion enabled bioreactor by sandwiching culture cells between two filter membranes. Any analyte generated in bioreactor 101 can then be continuously sampled/measured using the fluidic paper system.

Figure 8:
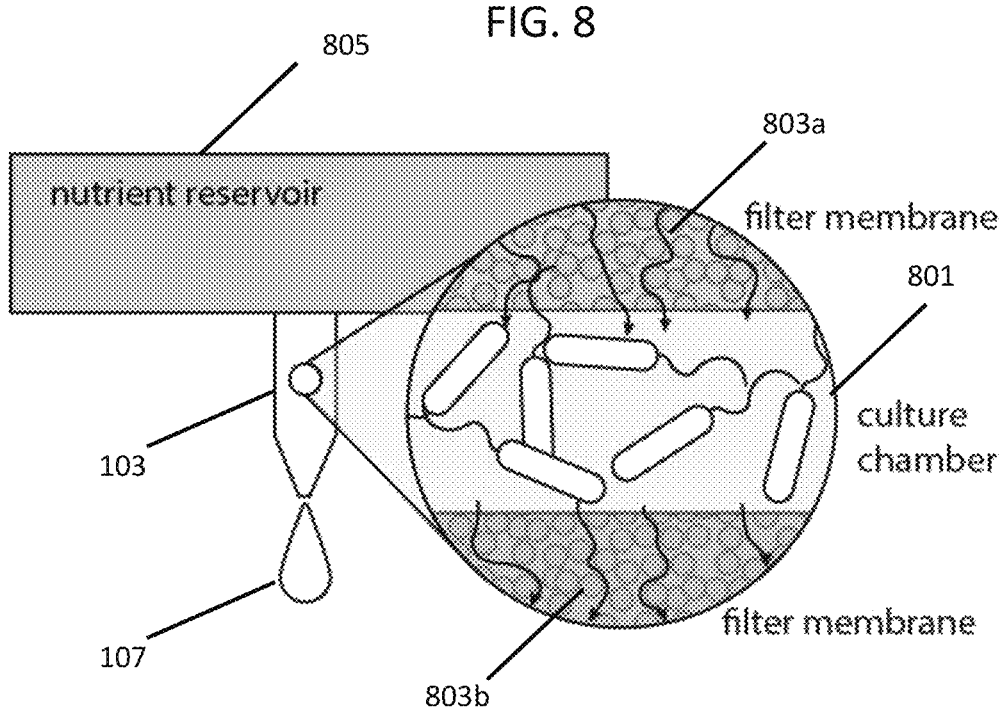
FIG. 8 is a diagram illustrating a sample dispenser including a culture chamber according to some embodiments of inventive concepts.

According to some embodiments illustrated in FIG. 8, bioreactor 101 may be combined with a dispenser 103 provided as a droplet dispensing needle. A culture chamber 801 (also referred to as a culture environment) may be housed between two filter membranes 803a and 803b embedded within the droplet dispensing needle. A nutrient reservoir 805 above the dispensing needle 103 may allow continuous perfusion and droplet generation. Nutrient reservoir 805 may be provided between bioreactor 101 and dispenser 103, or nutrient reservoir 805 may be included in bioreactor 101.

According to some embodiments, sample dispenser 103 may be provided using a passive orifice 'leaking' fluid from bioreactor 101 via surface tension of continuous droplet contact with absorbent material of sample collection film 105. According to some other embodiments, sample dispenser 103 may be provided using active dispensing (e.g., extrusion) via pneumatic and/or hydraulic pumps and/or positive displacement devices. Spatial distribution of reactor fluid and likewise its contents could be simple or complex. The fluid could be allowed to flow into the absorbent material of sample collection film 105 generally undirected, or directed via an articulating nozzle, pneumatic displacement, electrostatic displacement, or mechanical displacement.

According to some embodiments, sample collection film 105 may be provided using an absorbent material 201 (i.e., a layer of an absorbent material) backed by a layer of an impermeable barrier material 203 (i.e., a layer of an impermeable material). Suitable materials for the absorbent material may include 3D surfaces which capture liquid and/or particulates. Examples of absorbent materials may include (but are not limited to) fibrous meshes, sintered particles, micromachined surfaces, and/or lithographically formed surfaces. Pore size, or capture space size, of an absorbent material 3D surface may be provided to be consistent with particulate size and desired capture volume of liquid components being dispensed. According to some embodiments, the impermeable barrier material 203 may be a distinctly different material from the absorbent material. For example, the absorbent material may be a glass fiber, and the impermeable material may be wax. According to some other embodiments, impermeable barrier material 203 may be a functionalized version of the absorbent material making it repulsive to the liquid component. For example, the hydrophobic coated regions of the absorbent material may provide barriers to an aqueous liquid component of a sample. According to still other embodiments, impermeable barrier material 203 may be provided using a combination of a functionalized version of the absorbent material and a material distinctly different than the absorbent material. For example, impermeable barrier material 203 may be provided using wax infilled glass fiber to form 'walls' separating frames of sample collection film 105. According to some embodiments, sample collection film 105 may be provided using film layering using varying combinations of absorbent material, porous membranes, and impermeable materials, and such layering can be used to expand uses/applications of sample collection devices disclosed herein. Each of these layers may be selectively functionalized, further expanding use.

Functionalization of layers/surfaces of sample collection film 105 may provide optional expansion of the absorbent material to perform additional functions, such as segregation of biomolecules of interest or disinterest, and/or to perform additional functions, such as enhanced capture of particulate constituents from the liquid. As each droplet is received on a sample region of sample collection film 105, the fluid may take some time to fully swell the paper fluidic system and may thus spend different amounts of time in/on different areas of the sample region. By doping reagents in a specific order, chemical reactions may occur. In the example shown in FIG. 9, an immunoassay may be provided that can lock the measured antigen in place for future readout. This feature of the variable reaction area can control the incubation time of the antigen exposed to each reagent. Since these assays are developed on a continuous roll, the evolution of the cell culture environment over time can be measured.

Figure 9:
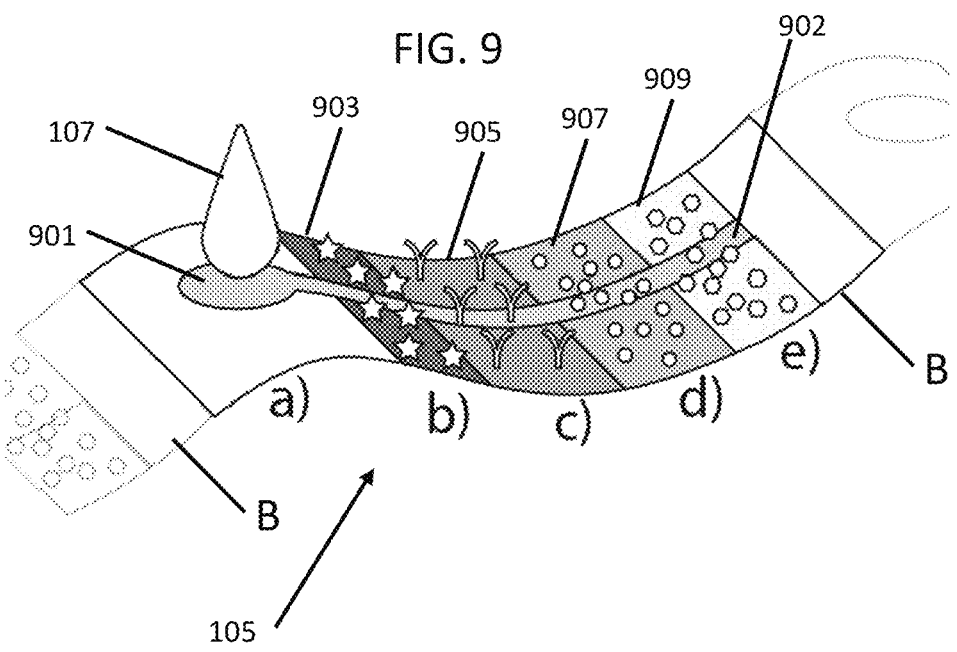
FIG. 9 is a plan view illustrating a sample collection film for fluidic immunoassay testing according to some embodiments of inventive concepts.

FIG. 9 illustrates embodiments of sample collection film 105 including a fluidic test section/frame for fluidic immunoassay testing. In FIG. 9, liquid sample 107 droplet containing an antigen(s) of interest is dropped onto the input pad 901, and fluid of liquid sample 107 is drawn from pad 901 via capillary action along channel 902 across discrete sections of the sample frame coated in lyophilized conjugates to complete an immunoassay. As fluid of liquid sample 107 moves through a section 903, the antigen(s) is tagged with a lyophilized detector protein. As the fluid of sample 107 moves through section 905, lyophilized antibodies specific for the antigen(s) of interest sequester the target. As the fluid of sample 107 moves through section 907, a fixative chemical may lock captured analytes in place. As the fluid of sample 107 moves through section 909, a fixative quenching agent may slow/halt fixation. Moreover, impermeable barriers B may separate different sample frames along sample collection film 105. In addition, the immunoassay may be enabled by integration of in-line optical sensing to device or preserved for ex situ measurement.

According to some embodiments of inventive concepts, the absorbent sample collection film 105 may be used to create an historical record of bio-samples that can be replayed at a later time. Such historical records may be useful to record biological evolution such as bacterial evolution in laboratory microgravity experiments, and/or to record pathogenesis in high contact communities (e.g., shipboard) where unpredictable outbreaks could be given a passive solid-state pathogenic historical record by sampling central wastewater output.

Sample collection devices and/or films according to some embodiments of inventive concepts may thus provide phase separation of biomass from culture liquid to capture bulk biologics (e.g., bacteria, etc.). With such films, a sample may be absorbed into a 3D absorbent material through capillary action. Moreover, drum-based microfluidics can be integrated into the sample collection film for continuous monitoring, and/or bio-sample storage may be automated/organized.

According to some embodiments of inventive concepts discussed above, sample dispenser 103/103' may dispense liquid samples from a bioreactor 101. Bioreactor 101, for example, may be used for experiments conducted in space (e.g., in low-earth orbit), and the sample collection device may be used to automatically capture and store samples for return to earth where analysis may be performed at a later time. In such embodiments, dispensing may be performed based on at least one of surface tension and/or pumping.

Figure 10:
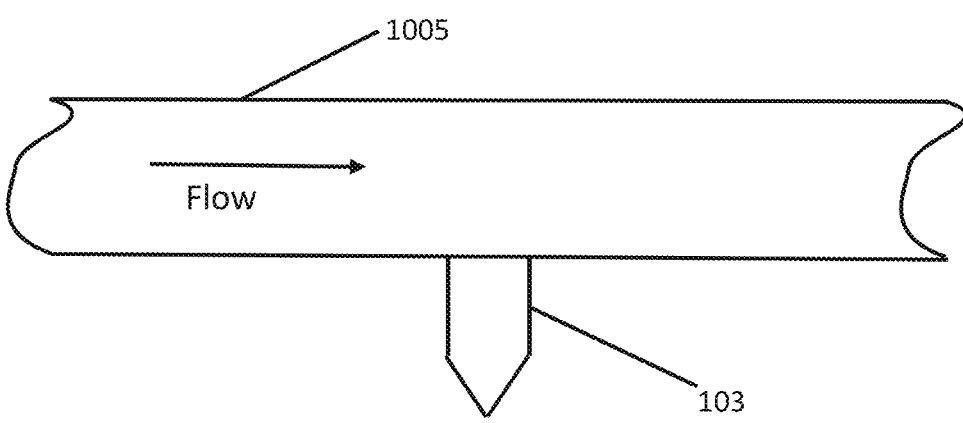
FIG. 10 is a diagram illustrating a sample dispenser coupled with a pipe according to some embodiments of inventive concepts.

According to other embodiments, other sources may be used. As shown in FIG. 10, for example, sample dispenser 103 may dispense samples from a pipe 1005 (e.g., a sewer pipe) carrying a flow of material, with elements below sample dispenser 103 being the same as discussed above with respect to FIGS. 1A, 4, 5, 6, and/or 7. In such embodiments, the sample collection device may be used to provide solid-state biosampling for eDNA monitoring to provide forensic analysis of water quality and/or pathogenesis. For example, the sample collection device may be used to monitor for pathogens in land or ship based sewer systems. In such terrestrial embodiments, dispensing may be performed based on at least one of surface tension, pumping, and/or gravity.

The terminology used herein is for the purpose of describing particular embodiments only and is not intended to be limiting of inventive concepts. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof. The term "and/or" includes any and all combinations of one or more of the associated listed items.

Spatially relative terms, such as "beneath," "below," "lower," "above," "upper," and the like, may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations), and the spatially relative descriptors used herein may be interpreted accordingly.

It will be understood that, although the terms first, second, third, etc. may be used herein to describe various elements, these elements should not be limited by these terms. These terms are only used to distinguish one element from another element. Thus, a first element discussed below could be termed a second element without departing from the scope of the present inventive concepts.

It will also be understood that when an element is referred to as being "on" or "connected to" another element, it can be directly on or connected to the other element, or intervening elements may be present. In contrast, when an element is referred to as being "directly on" or "directly connected to" another element, there are no intervening elements present. Moreover, if an element is referred to as being "on" another element, no spatial orientation is implied such that the element can be over the other element, under the other element, on a side of the other element, etc.

Embodiments are described herein with reference to cross-sectional and/or perspective illustrations that are schematic illustrations of idealized embodiments (and intermediate structures). As such, variations from the shapes of the illustrations as a result, for example, of manufacturing techniques and/or tolerances, are to be expected. Thus, embodiments should not be construed as limited to the particular shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of the present inventive concept.

Unless otherwise defined, all terms (including technical and scientific terms) used herein have the same meaning as commonly understood by one of ordinary skill in the art to which the inventive concepts herein belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

While inventive concepts have been particularly shown and described with reference to examples of embodiments thereof, it will be understood that various changes in form and details may be made therein without departing from the spirit of the following claims.

The invention claimed is:

1. A method of collecting liquid samples, the method comprising:

unrolling a portion of a sample collection film from a first reel to a position adjacent a sample dispenser;

dispensing a liquid sample from the sample dispenser onto the portion of the sample collection film;

dispensing at least one reagent onto the portion of the sample collection film before and/or after dispensing the liquid sample onto the portion of the sample collection film, wherein the at least one reagent is dispensed onto the portion of the sample collection film after unrolling the portion of a sample collection film from the first reel to the position adjacent the sample dispenser; and after dispensing the liquid sample and the at least one reagent onto the portion of the sample collection film, rolling the portion of the sample collection film onto a second reel.

2. The method of claim 1, wherein the sample collection film comprises a continuous layer of an absorbent material.

3. The method of claim 2, wherein the sample collection film comprises a continuous layer of a barrier material with the continuous layer of the absorbent material on the continuous layer of the barrier material, and wherein dispensing comprises dispensing the liquid sample on the continuous layer of the absorbent material.

4. The method of claim 2, wherein the portion of the sample collection film is a first portion of the sample collection film, and wherein the liquid sample is a first liquid sample, the method further comprising:

unrolling a second portion of the sample collection film from the first reel to the position adjacent the sample dispenser;

after dispensing the first liquid sample, dispensing a second liquid sample from the sample dispenser onto the second portion of the sample collection film; and after dispensing the second liquid sample, rolling the second portion of the sample collection film onto the second reel.

5. The method of claim 2, wherein unrolling comprises sequentially unrolling first and second portions of the sample collection film from the first reel to the position adjacent the sample dispenser, wherein dispensing comprises continuously dispensing the liquid sample from the sample dispenser onto and between the first and second portions of the sample collection film, and wherein rolling comprises sequentially rolling the first and second portions of the sample collection film onto the second reel.

6. The method of claim 1, wherein the sample collection film comprises a continuous layer of a barrier material and a plurality of spaced apart frames of absorbent material on the continuous layer of the barrier material, wherein the portion of the sample collection film comprises a first frame of the plurality of frames, wherein unrolling the portion of the sample collection film comprises unrolling the first frame from the first reel to the position adjacent the sample dispenser, and wherein dispensing comprises dispensing a first liquid sample from the sample dispenser onto the first frame of absorbent material.

7. The method of claim 6, wherein a second portion of the sample collection film comprises a second frame of the plurality of frames of absorbent material, the method further comprising:

unrolling the second frame of absorbent material from the first reel to the position adjacent the sample dispenser;

after dispensing the first liquid sample, dispensing a second liquid sample from the sample dispenser onto the second frame of absorbent material; and after dispensing the second liquid sample onto the second frame of absorbent material, rolling the second portion of the sample collection film onto the second reel.

8. The method of claim 6, wherein a portion of a continuous layer of the barrier material between two of the plurality of frames includes perforations.

9. The method of claim 1 further comprising:

after dispensing the liquid sample onto the portion of the sample collection film, applying a barrier film to the portion of the sample collection film, wherein rolling comprises rolling the portion of the sample collection film and the barrier film onto the second reel.

10. The method of claim 1, wherein the first reel comprises a first spool and a pair of first rims extending from opposite sides of the first spool wherein a fresh portion of the sample collection film is rolled on the first spool between the first rims, and/or wherein the second reel comprises a second spool and a pair of second rims extending from opposite sides of the second spool wherein an exposed portion of the sample collection film is rolled on the second spool between the second rims.

11. The method of claim 1, wherein dispensing comprises dispensing the liquid sample from at least one of a bioreactor and/or a pipe.

12. The method of claim 1 further comprising:

mixing at least one reagent with the liquid sample before dispensing the liquid sample onto the portion of the sample collection film.

13. The method of claim 1, wherein dispensing comprises dispensing the liquid sample from the sample dispenser onto the portion of the sample collection film based on at least one of surface tension, gravity, and/or pumping.

14. A sample collection device comprising:

a film dispenser configured to receive a first reel wherein a sample collection film is rolled on the first reel;

a film receiver configured to receive a second reel;

a driver coupled with the film receiver wherein the driver is configured to turn the second reel to unroll a portion of the sample collection film from the first reel to a dispensing position and then onto the second reel;

a sample dispenser configured to dispense a liquid sample onto the portion of the sample collection film at the dispensing position; and a reagent dispenser configured to dispense at least one reagent onto the portion of the sample collection film before and/or after dispensing the liquid sample onto the portion of the sample collection film, wherein the at least one reagent is dispensed onto the portion of the sample collection film after unrolling the portion of a sample collection film from the first reel to the position adjacent the sample dispenser.

15. The sample collection device according to claim 14, wherein the film dispenser comprises a first hub configured to detachably mate with the first reel allowing the first reel to turn when detachably mated with the first hub, wherein the film receiver comprises a second hub configured to detachably mate with the second reel allowing the second reel to turn when detachably mated with the second hub, and wherein the driver comprises a motor configured to turn the second reel by turning the second hub when detachably mated with the second reel.

16. The sample collection device of claim 14, wherein the sample collection film comprises a continuous layer of an absorbent material.

17. The sample collection device of claim 16, wherein the sample collection film comprises a continuous layer of a barrier material with the continuous layer of the absorbent material on the continuous layer of the barrier material, and wherein the sample dispenser is configured to dispense the liquid sample on the continuous layer of the absorbent material.

18. The sample collection device of claim 17, wherein the portion of the sample collection film is a first portion of the sample collection film, wherein the liquid sample is a first liquid sample, wherein the driver is configured to turn the second reel to unroll a second portion of the sample collection film from the first reel to the dispensing position adjacent the sample dispenser, wherein the sample dispenser is configured to dispense a second liquid sample onto the second portion of the sample collection film after dispensing the first liquid sample, and wherein the driver is configured to turn the second reel to roll the first portion of the sample collection film onto the second reel after the sample dispenser dispenses the first liquid sample and to roll the second portion of the sample collection film onto the second reel after the sample dispenser dispenses the second liquid sample.

19. The sample collection device of claim 14, wherein the liquid sample is a first liquid sample, wherein the sample collection film comprises a continuous layer of a barrier material and a plurality of spaced apart frames of absorbent material on the continuous layer of the barrier material, wherein the portion of the sample collection film comprises a first frame of the plurality of frames of absorbent material, wherein the driver is configured to unroll the first frame of absorbent material from the first reel to the dispensing position, wherein the sample dispenser is configured to dispense the first liquid sample onto the first frame of absorbent material, and wherein a portion of the continuous layer of the barrier material between the first frame of the absorbent material and a second frame of the absorbent material is perforated.

* * * * *